United States Patent

Milewicz

[11] Patent Number: 6,010,118
[45] Date of Patent: Jan. 4, 2000

[54] MEDICAL HUMIDIFIER

[75] Inventor: Edek Milewicz, Queensland, Australia

[73] Assignee: William A. Cook Australia Pty, Ltd., Brisbane, Australia

[21] Appl. No.: 08/991,759

[22] Filed: Dec. 16, 1997

[30] Foreign Application Priority Data

Dec. 18, 1996 [AU] Australia .................... PO4254

[51] Int. Cl.⁷ .................... B01F 3/04
[52] U.S. Cl. .................... 261/142; 96/371; 128/203.27; 128/204.13; 128/205.12; 261/96; 261/105
[58] Field of Search .................... 261/130, 142, 261/96, 105; 128/203.27, 203.26, 204.13, 205.12; 96/294, 371

[56] References Cited

U.S. PATENT DOCUMENTS

| | | | |
|---|---|---|---|
| 2,057,353 | 10/1936 | Whittemore, Jr. | 128/203.27 |
| 3,102,537 | 9/1963 | Bartlett, Jr. | 128/204.13 |
| 4,121,583 | 10/1978 | Chen | 128/203.27 |
| 4,225,542 | 9/1980 | Wall et al. . | |
| 4,674,494 | 6/1987 | Wiencek . | |
| 4,748,314 | 5/1988 | Desage | 261/142 |
| 4,773,410 | 9/1988 | Blackmer et al. | 128/203.27 |
| 4,774,032 | 9/1988 | Coates et al. | 128/204.13 |
| 4,825,863 | 5/1989 | Dittmar et al. | 128/203.27 |
| 5,255,674 | 10/1993 | Oftedal et al. | 128/203.27 |
| 5,392,770 | 2/1995 | Clawson et al. | 128/203.27 |

FOREIGN PATENT DOCUMENTS

| | | | |
|---|---|---|---|
| 74564 | 4/1976 | Australia | 128/203.27 |
| 8901037 | 4/1992 | Belgium . | |
| 2810325 | 9/1979 | Germany . | |
| 3927594 | 6/1990 | Germany . | |
| 9616689 | 6/1996 | WIPO . | |

*Primary Examiner*—C. Scott Bushey
*Attorney, Agent, or Firm*—Richard J. Godlewski

[57] ABSTRACT

A humidified medical gas supply apparatus to supply gas such as carbon dioxide for laparoscopic surgery includes a gas supply, a supply controller, and a gas supply tube which has a humidification chamber mounted into it. The chamber has a dampened gas-pervious medium and an electrical heating element. The electrical element may extend along the gas supply tube and be wound around the medium within the chamber. A control controls an electrical supply to the electrical heating element to vary the electrical supply dependent upon a gas flow rate in the supply tube.

18 Claims, 4 Drawing Sheets

MEDICAL HUMIDIFIER

TECHNICAL FIELD

This invention relates to a gas humidification device particularly useful in relation to medical applications.

The present invention will be particularly discussed in relation to supply of gas for laparoscopic surgery but the invention is also applicable to anaesthesia and other medical procedures in which the delivery of gas to body cavities or organs is required.

BACKGROUND OF THE INVENTION

During laparoscopic surgery carbon dioxide gas is insufflated into the peritoneal cavity to create a working space between the interior abdominal wall and the abdominal organs. Other gases than carbon dioxide have also been used. An item of medical equipment known as an insufflator unit is used to regulate and control the delivery of gas between a gas supply, such as from a gas cylinder, and the patient.

Delivery of gas which is at high pressure in the gas cylinder to the low pressure environment of the patient necessitates gas expansion within the insufflator unit. The expansion of this gas results in considerable heat being lost from the gas and hence there is the potential for gas to be delivered to the patient at somewhat less than room or body temperature. Testing has shown that gas temperature can be as low as 14° C. compared to the standard body temperature of 38° C.

There has been some clinical experimentation performed to evaluate whether heating the gas used during laparoscopic surgery provides benefits to the patient. These benefits have been found to consist of less post-surgical pain and less lowering of core body temperature during longer procedures. Insufflation units have been proposed, therefore, which have the ability to deliver heated gas to the patient. This is seen as a significant improved feature over other units available. The delivery of heated gas is normally achieved not only by heating the gas within the insufflator unit but supplementing this heating by heating the gas in the line between the insufflator and the patient. One such device is known as a Cook Medical Technology LINS-1000 Insufflator which provides a disposable heated gas line apparatus to enable delivery of heated gas to a patient.

More recently, however, it has been proposed that humidification of the gas being supplied to a patient should also be carried out. Research has ascertained that once dry heated gas enters the peritoneal cavity, which is a moist environment, considerable body heat is used to humidify this heated but dry gas.

U.S. Pat. No. 5,411,474 discloses a humidification apparatus for insufflation gas for medical procedures. A temperature sensor is used to measure the temperature of the humidified gas at the outlet of the humidifier. By this means, there is an attempt to maintain a constant temperature of the humidified gas as it enters the patient but because the gas flow rate may vary there is no control of the degree of humidification. As gas flow rates may vary from one liter per minute to twenty five liters per minute, the humidity of the gas such as carbon dioxide may not be at an optimum or preferred level.

It is the object of this invention to provide a humidification arrangement for gas supplies to a patient whether the gas supply be for the purpose of laparoscopic surgery or other procedures which will overcome some of the above problems or at least provide the public with a useful alternative.

SUMMARY OF THE INVENTION

In one form, the invention resides in a medical gas humidifier comprising a gas supply tube extending from an inlet end to an outlet end and a humidification chamber mounted into the tube, the humidification chamber having a gas passage therethrough and a gas-pervious medium within the chamber and interposed in the gas passage, the medium being water absorbent, a heating element extending along and within at least a portion of the gas supply tube and wound around the gas-pervious medium within the chamber.

It will be seen that with the gas passing through the chamber and the gas-pervious medium as the gas is heated, it will evaporate some moisture in the water-absorbent medium and carry this through to the patient. The chamber may include some means to admit water, such as a water injection port, or it may be supplied already with water absorbed onto the medium as a disposable unit. The water injection port may be at an exit end of the humidification chamber.

Preferably, the gas-pervious medium comprises an inlet baffle with a gas entry port, a perforated tube extending to an outlet baffle and a wadding around the perforated tube, the gas passage extending through the gas entry port into the perforated tube, through the perforations thereof, through the wadding and past the outlet baffle.

The heating element may comprise a resistance heating wire which extends along the length of the gas supply tube from a gas supply and heater control box, through the chamber and continuing on in the tube to the outlet end.

The medical gas humidifier may include thermal insulation around the chamber to prevent loss of heat from the chamber.

In an alternative form, the invention resides in a humidified medical gas supply apparatus comprising a supply controller, a first gas supply tube extending from the supply controller to a humidification chamber, and a second gas supply tube extending from the humidification chamber to outlet end, the humidification chamber having a gas passage therethrough and a gas-pervious medium within the chamber and interposed in the gas passage, the medium being water absorbent, an electrical heating element extending along and within at least a portion of the first and second gas supply tubes and wound around the gas-pervious medium within the chamber, and control means in the supply controller to control an electrical supply to the electrical heating element, whereby to vary the electrical supply dependent upon a gas flow rate in the supply controller.

The gas-pervious medium may comprise an inlet baffle with a gas entry port, a perforated tube extending to an outlet baffle and a wadding around the perforated tube, the gas passage extending through the gas entry port into the perforated tube, through the perforations thereof, through the wadding and past the outlet baffle.

The chamber may include a water injection port preferably at an exit end of the humidification chamber.

The heating element may comprise a resistance heating wire which extends along the length of the first gas supply tube from the controller through the humidification chamber and continuing on in the second gas supply tube to the outlet end.

There may be further included thermal insulation around the chamber to prevent loss of heat from the chamber.

The gas supplied to the apparatus may be carbon dioxide.

There may be a filter in the first gas supply tube upstream of the humidification chamber.

Preferably, the gas humidifier device according to this invention may be incorporated in a disposable unit for laparoscopic surgery or similar procedures.

This then generally discloses the invention, but to assist with understanding, reference will now be had to the accompanying drawings which show a preferred embodiment of the drawings.

DETAILED DESCRIPTION

Figure 1:
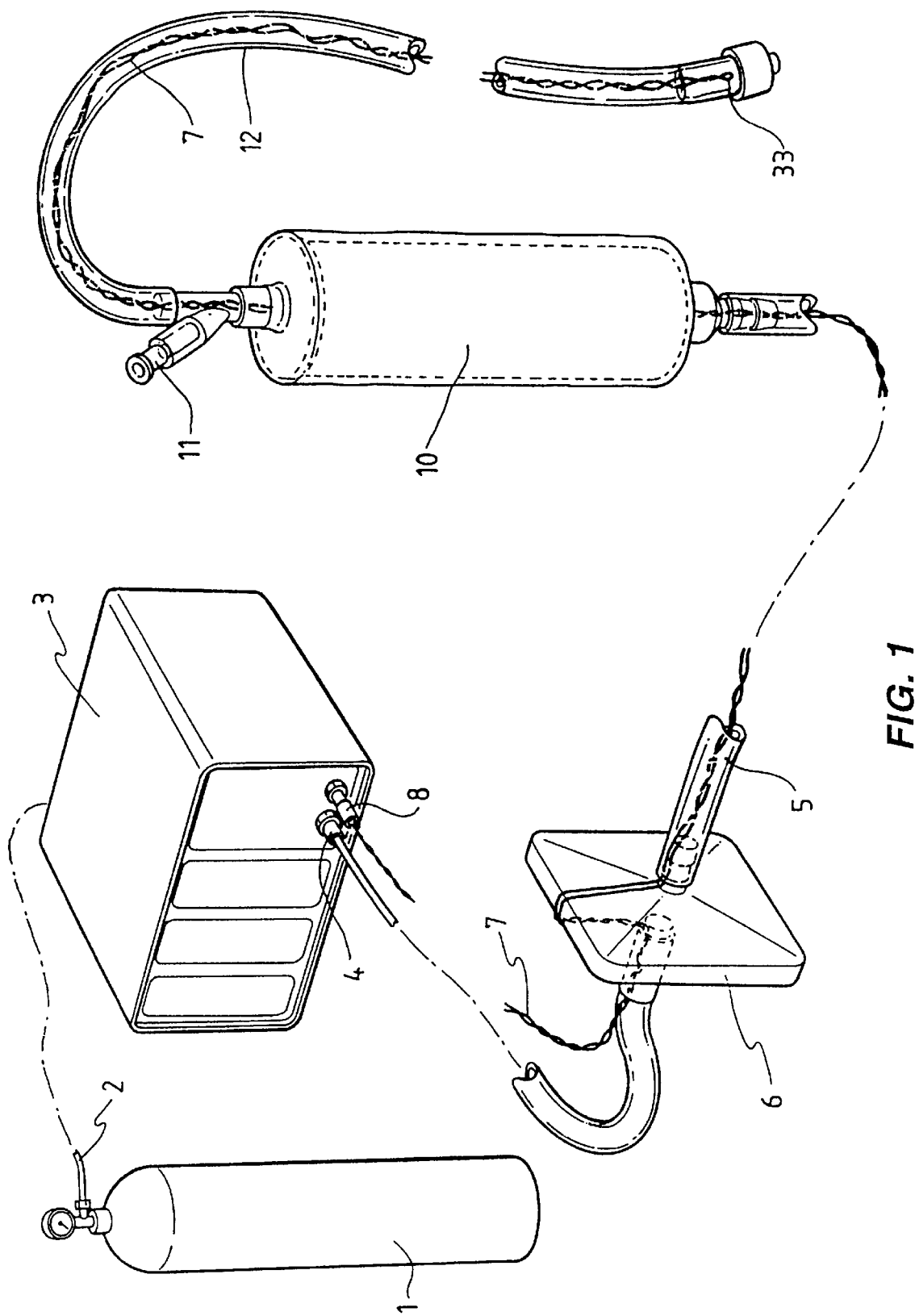
FIG. 1 shows a schematic view of a gas supply system for laparoscopic surgery including heating and humidification according to the present invention.

Now looking more closely at the drawings and in particular FIG. 1, it will be seen that gas can be supplied from a gas supply tank 1 by a gas supply tube 2 to supply controller or insufflator 3. The insufflator 3 has controllers to control gas flow rate and pressure and heating of the gas supply. Generally, the amount of heating supplied is dependent on the flow rate of gas and the time that the heating unit has been on. Gas is provided through port 4 in the insufflator to a first gas supply tube 5, which passes through an optional filter 6 so that the supplied gas is clean before it enters a patient. A heater wire 7 is plugged into a heater socket 8 in the insufflator unit and the wire is retained on the outside of the first gas supply tube until after it passes over the filter unit 6 and then it enters the first gas supply tube and extends down the length of the first gas supply tube 5. An electrical current is passed through the wire 7 and by resistance heating the gas in the tube 5 is heated.

The humidification chamber 10 of the present invention is placed in the first gas supply tube 5 and includes a liquid entry port 11 at an exit end of the humidification chamber 10. The humidification chamber 10 will be discussed in more detail in relation to FIG. 2. The second gas supply tube 12 extending beyond the humidification chamber extends to suitable equipment such as a port for enabling the heated and humidified gas to be supplied to a patient. The heating wire 7 also extends along substantially the full length of the second gas supply tube 12.

Figure 2:
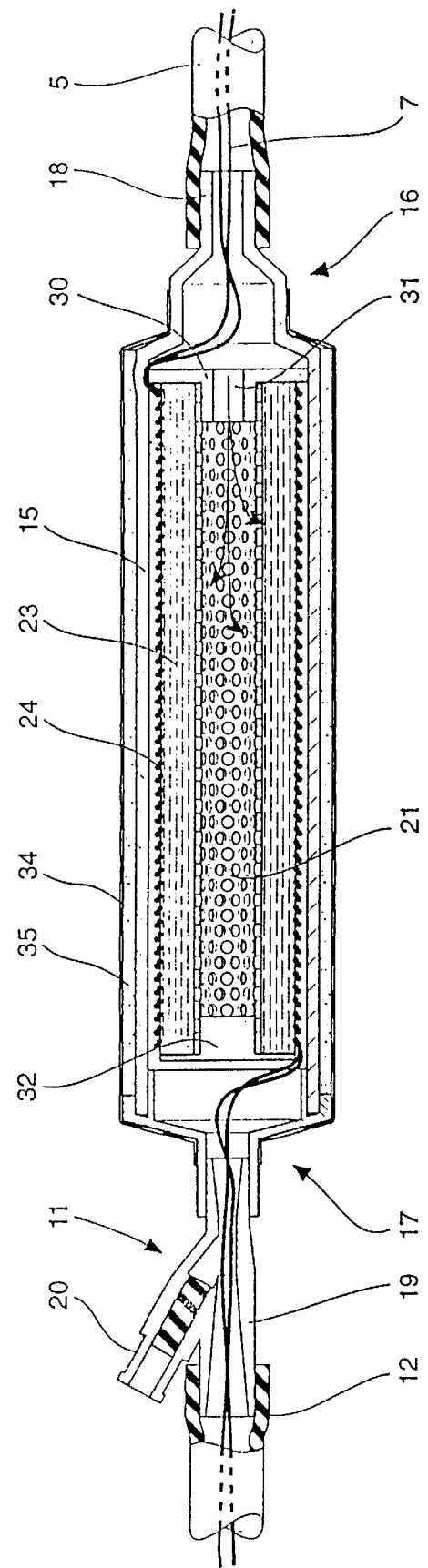
FIG. 2 shows a longitudinal cross-sectional view of a humidification chamber according to a first embodiment of the present invention.
Figure 3:
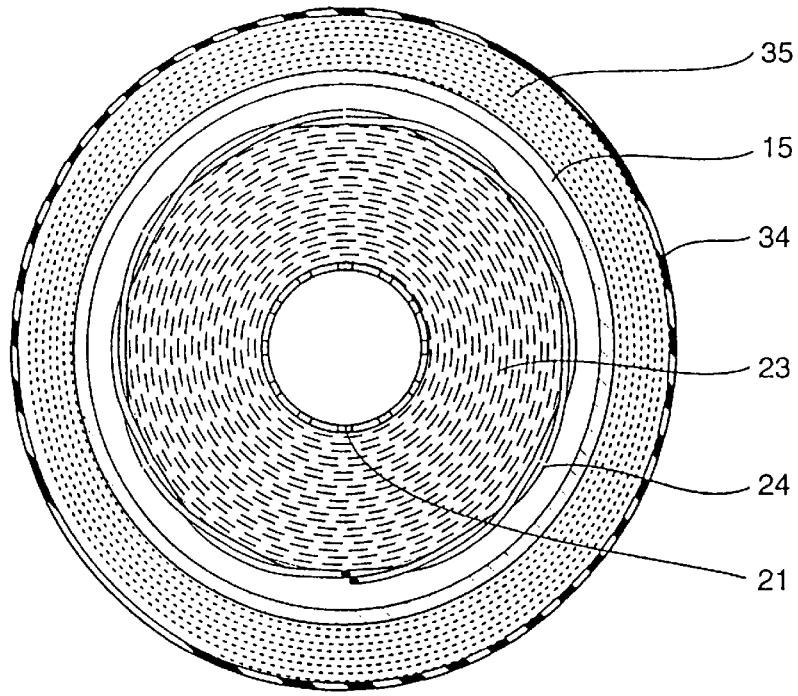
FIG. 3 is a transverse cross-sectional view of the humidification chamber of the embodiment shown in FIG. 2.

Now looking at the humidification chamber shown in detail in FIG. 2 and FIG. 3, it will be seen that the humidification chamber comprises an elongate chamber defined by an outer wall 15 which extends from an inlet end 16 to an outlet end 17. The first gas supply tube 5 connects to a socket 18 at the inlet end and the second gas supply tube 12 connects to a fitting 19 at the end 17 for delivery of warmed, humidified gas to a patient. A side port 20 is provided at the end 17 for the addition of water to the humidifier as required. The side port 20 has an elastomeric seal through which a hypodermic needle may be inserted to enable extra water to be added if required.

Around the elongate humidification chamber is an insulation layer 35 to prevent loss of heat from the humidification chamber. The insulation layer 35 is held in place by a shrink-wrap sleeve 34 over the insulation layer. The insulation layer is preferably a continuous band of a foil-backed, felted fabric wound around the chamber so that there are at least three layers.

The internal construction of this embodiment of the humidifier comprises an inlet baffle 30 with an aperture 31. The inlet baffle 30 fits tightly against the outer wall 15 to prevent gas flow around the outside of the inlet baffle. An outlet baffle 32 does not fit tightly against the wall 15 so that gas can flow past the outlet baffle 32. A perforated metal tube core 21 extends from the inlet baffle 30 to the outlet baffle 32 and is supported on projections on the respective baffles. The aperture 31 allows gas to pass through the inlet baffle into the tube core 21. A layer of water absorbent and gas permeable gauze 23 is wound over the perforated metal tube core 21 and then a winding of wire 24 is wound around the layer of gauze 23. The electrical heating wire 24 is a continuation of the heating wire 7 as shown in FIG. 1.

The gas permeable gauze is preferably a high absorbency cotton swab wound onto the core 21 to give a radial thickness of gauze of approximately 5 mm. This may be provided by approximately 16 thicknesses of swab over the perforated core 21.

The electrical heating wire 7, 24 may be a pair of wires joined at the end 33 or a single wire from the heater socket 8 extending the full length of the first and second tubes 5 and 12 and back again to the heater socket 8 as shown in FIG. 1.

It has been found that the amount of water which is necessary to be provided, such as by being injected into the humidification chamber through the side port 20, may be relatively small, for instance, in the region of 20 mls, and this amount of water moistens the gauze sufficiently to be used for a relatively long laparoscopic procedure.

Preferably, the heated gas line with humidification chamber delivers gas from the chamber at approximately 40° C. and 98% humidity.

Figure 4:
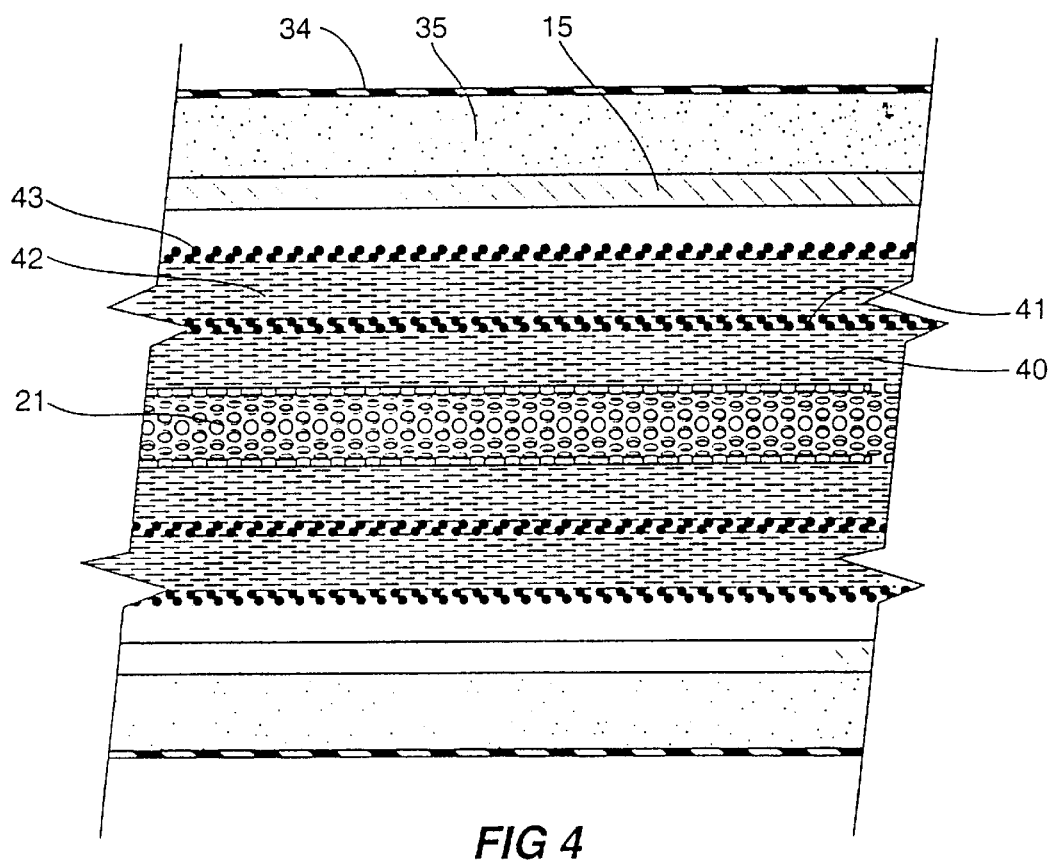
FIG. 4 is a part longitudinal cross-sectional view of an alternative embodiment of humidification chamber according to the invention.

FIG. 4 shows an alternative embodiment of construction of the humidification chamber. In this drawing, items with the same construction as in FIGS. 2 and 3 have the same reference numerals. In this embodiment, the perforated tube 21 has a first layer of high absorbency and air permeable gauze 40 wound around the tube 21 and then a first winding of electrical heating wire 41. There is next a second winding of high absorbency and air permeable gauze 42 and then around that a second winding of electrical heating wire 43. As in the earlier embodiment, the electrical heating wires 7, 41, and 43 are continuous.

Although the dimensions of a medical gas humidifier may be selected according to any required gas supply rate, in one preferred embodiment, the first gas supply tube 5 may be 2.4 meters long, the second gas supply tube 12 may be 30 cm long, and the total length of electrical heating wire may be 17 meters folded and twisted into a length of 8.4 meters. This gives a length of coiled portion within the humidification chamber of about 5.5 meters. Preferably, the wire is 26 AWG Kynor insulated wire.

The amount of heating supplied to the gas tubes and the humidifier is calculated from the amount of gas flowing and the period it has been flowing. Within the insufflation 3, the controller for the electricity supplied to the heater wire may act upon gas flow rate to switch on and off the electricity. This switching on and off may be termed the duty cycle with continuously on being 100% duty cycle. Approximately 30% of the heating occurs in the first tube, 65% in the humidification chamber, and 5% in the second tube.

At 100% duty cycle, the electrical heating wire dissipates 5 watts in the first tube, 10.5 watts in the humidification chamber, and 1 watt in the second tube. The duty cycle varies with the flow of carbon dioxide, but the ratio of each section remains constant.

Figure 5:
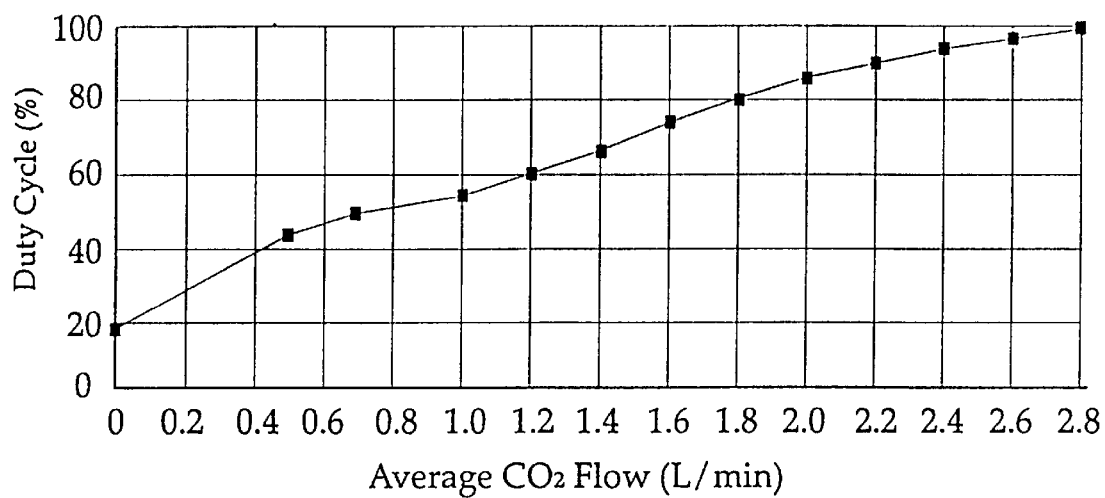
FIG. 5 is a graph showing a heater duty cycle versus gas flow rate for one embodiment of humidification apparatus according to the invention.

FIG. 5 shows a graph of duty cycle for the electricity supply to the heater wire 7, 24 as a function of gas flow rate through the supply controller 3. It will be noted that at no flow of gas the heater is supplied with about 18% of maximum power to generally warm the unit and prepare it for gas supply.

As discussed earlier, the delivery of gas to body cavities or organs often may benefit from heating and or humidification. The development of the device according to this invention would seem to have other uses apart from laparoscopic insufflation. These may include the delivery of anaesthesia gases during surgery or for respiratory conditions. Gases other than carbon dioxide may be used. Further, the design of the chamber allows the injection of substances other than simply sterile water, and one likely adjunct may be the addition of local anaesthetic to the sterile water. The benefit of this particular use may be to provide a systemic effect of local anaesthesia to the peritoneal cavity during surgery and hence much reduced post-procedural pain.

Throughout this specification, various indications have been given as to the scope of the invention; however the invention is not limited to these, but may reside in two or more of these combined together. The examples are given for illustration only and not for limitation.

What is claimed is:

1. A medical gas humidifier comprising a gas supply tube extending from an inlet end to an outlet end and a humidification chamber mounted into the tube, the humidification chamber having a gas passage therethrough and a gas-pervious medium within the chamber and interposed in the gas passage, the medium being water absorbent, a heating element extending along and within at least a portion of the gas supply tube and wound around the gas-pervious medium within the chamber.

2. A medical gas humidifier as in claim 1, wherein the gas-pervious medium comprises an inlet baffle with a gas entry port, a perforated tube extending to an outlet baffle and a wadding around the perforated tube, the gas passage extending through the gas entry port into the perforated tube, through the perforations thereof, through the wadding and past the outlet baffle.

3. A medical gas humidifier as in claim 1, wherein the chamber includes a water injection port.

4. A medical gas humidifier as in claim 3, wherein the water injection port is at an exit end of the humidification chamber.

5. A medical gas humidifier as in claim 1, wherein the heating element is wound around the gas-pervious medium in the chamber.

6. A medical gas humidifier as in claim 1, wherein the heating element is partially within the gas-pervious medium and partially wound around the gas-pervious medium.

7. A medical gas humidifier as in claim 1, wherein the heating element comprises a resistance heating wire which extends along the length of the gas supply tube from a gas supply and heater control box, through the chamber, and continuing on in the tube to the outlet end.

8. A medical gas humidifier as in claim 1, further including thermal insulation around the chamber to prevent loss of heat from the chamber.

9. A humidified medical gas supply apparatus comprising a supply controller, a first gas supply tube extending from the supply controller to a humidification chamber and a second gas supply tube extending from the humidification chamber to outlet end, the humidification chamber having a gas passage therethrough and a gas-pervious medium within the chamber and interposed in the gas passage, the medium being water absorbent, an electrical heating element extending along and within at least a portion of the first and second gas supply tubes and wound around the gas-pervious medium within the chamber, and control means in the supply controller to control an electrical supply to the electrical heating element whereby to vary the electrical supply dependent upon a gas flow rate in the supply controller.

10. A humidified medical gas supply apparatus as in claim 9, wherein the gas-pervious medium comprises an inlet baffle with a gas entry port, a perforated tube extending to an outlet baffle and a wadding around the perforated tube, the gas passage extending through the gas entry port into the perforated tube, through the perforations thereof, through the wadding and past the outlet baffle.

11. A humidified medical gas supply apparatus as in claim 9 wherein the chamber includes a water injection port.

12. A humidified medical gas supply apparatus as in claim 11, wherein the water injection port is at an exit end of the humidification chamber.

13. A humidified medical gas supply apparatus as in claim 9, wherein the heating element comprises a resistance heating wire which extends along the length of the first gas supply tube from the supply controller, through the humidification chamber and continuing on in the second gas supply tube to the outlet end.

14. A humidified medical gas supply apparatus as in claim 9, wherein the heating element is wound around the gas-pervious medium in the chamber.

15. A humidified medical gas supply apparatus as in claim 9, wherein the heating element is partially within the gas-pervious medium and partially wound around the gas-pervious medium.

16. A humidified medical gas supply apparatus as in claim 9, further including thermal insulation around the chamber to prevent loss of heat from the chamber.

17. A humidified medical gas supply apparatus as in claim 9, further including a gas supply and a third gas supply tube extending from the gas supply to the supply controller and wherein the gas supply provides carbon dioxide.

18. A humidified medical gas supply apparatus as in claim 9, further comprising a filter in the first gas supply tube upstream of the humidification chamber.

* * * * *